US005896856A

United States Patent [19]

Frasier et al.

[11] Patent Number: 5,896,856

[45] Date of Patent: Apr. 27, 1999

[54] EMERGENCY AIR COOLING DEVICE

[76] Inventors: Robert J. Frasier, 1314 E. Poplar St., Stockton, Calif. 95205; Patrick R. Jones, 5740 Turtle Valley Dr., Stockton, Calif. 95207

[21] Appl. No.: 08/910,655

[22] Filed: Aug. 13, 1997

Related U.S. Application Data

[60] Provisional application No. 60/023,407, Aug. 14, 1996.

[51] Int. Cl.[6] ........ A61M 16/00

[52] U.S. Cl. ........ 128/204.15; 128/206.29

[58] Field of Search ........ 128/204.15, 204.16, 128/205.26, 206.29

[56] References Cited

U.S. PATENT DOCUMENTS

| | | | |
|---|---|---|---|
| 2,130,089 | 9/1938 | Hull | 128/204.15 |
| 2,920,622 | 1/1960 | Steel | 128/205.26 |
| 2,980,112 | 4/1961 | Snyder | 128/205.26 |
| 3,294,088 | 12/1966 | Boehmer et al. | 128/205.26 |
| 3,404,684 | 10/1968 | Brewer, Jr. et al. | 128/205.26 |
| 3,999,541 | 12/1976 | Tabor | 128/205.26 |
| 4,586,500 | 5/1986 | Glynn | 128/204.15 |
| 4,602,486 | 7/1986 | Weinstein | 128/205.26 |
| 4,635,629 | 1/1987 | Thorp et al. | 128/204.15 |
| 5,421,326 | 6/1995 | Rankin et al. | 128/201.21 |
| 5,482,031 | 1/1996 | Lambert | 128/204.16 |

FOREIGN PATENT DOCUMENTS

| | | | |
|---|---|---|---|
| 29119 | 12/1912 | United Kingdom | 128/204.15 |

*Primary Examiner*—Aaron J. Lewis
*Attorney, Agent, or Firm*—Gerald E. Linden

[57] ABSTRACT

A lightweight, compact breathing device for firefighters includes a housing having a one end for receiving hot air, a coolant storage cylinder disposed within the housing, an expansion valve in fluid communication with the coolant storage cylinder, a heat exchanger disposed within the housing having a one end in fluid communication with the expansion valve and having another opposite end, a coolant exhaust hose in fluid communication with the opposite end of the heat exchanger, and a mouthpiece in fluid communication with the housing. In use, the expansion valve is opened so that coolant flows from the coolant storage cylinder through the heat exchanger so that air passing through the housing from the one end to the mouthpiece through the heat exchanger is cooled by coolant passing from the coolant storage cylinder through the heat exchanger.

7 Claims, 2 Drawing Sheets

EMERGENCY AIR COOLING DEVICE

CROSS-REFERENCE TO RELATED APPLICATIONS

This is a continuation-in-part of commonly-owned, U.S. Provisional Patent Application No. 60/023,407 filed Aug. 14, 1996 by Frasier and Jones, incorporated by reference herein.

BACKGROUND OF THE INVENTION

A major cause of death among firefighters, particularly those fighting forest fires, is breathing super-heated air. The problem is that the firefighter's position may be overrun by fire and, although they are typically equipped with thermal shelters (heat-reflective tents), they are often injured (sometimes fatally) by breathing superheated air inside the shelter.

Many of the injuries sustained by fire fighters occur as a result of inhalation of super-heated air. In roughly half of all "entrapments" or "burn-over events", the fire fighters suffer significant damage to their lungs despite the protection of their Emergency Thermal Shelter, a heat reflective tent the fire fighter shelters in. When the grass or trees nearest the fire fighter burn, temperatures inside the shelter can exceed 200° for short periods of time.

What is needed is a breathing device that is lightweight compact, and that cools air prior to its being inhaled. The present invention is directed to such an air cooling device.

The following U.S. patents, incorporated by reference herein, disclose breathing devices:

U.S. Pat. No. 5,269,293 COOLING DEVICE FOR COOLING BREATHING GAS.

U.S. Pat. No. 5,222,489 SELF-REGULATING COOLED AIR BREATHING APPARATUS;

U.S. Pat. No. 4,821,711 PROTECTIVE BREATHING DEVICE;

U.S. Pat. No. 4,752,310 ADIABATIC HEATING AND COOLING PROCESS;

U.S. Pat. No. 4,635,629 BREATHING APPARATUS;

U.S. Pat. No. 4,611,589 DEVICE FOR REGENERATING RESPIRATORY BREATHING AIR;

U.S. Pat. No. 4,586,500 BREATHING DEVICE;

U.S. Pat. No. 4,314,566 AIR COOLER FOR SELF-CONTAINED BREATHING SYSTEM;

U.S. Pat. No. 4,300,547 RESPIRATOR HAVING MEANS FOR COOLING INHALATION AIR;

U.S. Pat. No. 4,294,244 RESPIRATOR WITH A COOLING DEVICE;

U.S. Pat. No. 4,251,994 AIR POWERED SOURCE FOR COOLED BREATHABLE AIR;

U.S. Pat. No. 4,188,947 BREATHING DEVICE HAVING A COOLANT CHAMBER;

U.S. Pat. No. 4,168,706 PORTABLE BREATHING SYSTEM;

U.S. Pat. No. 4,080,103 PORTABLE AIR COMPRESSOR SYSTEM FOR RESPIRATOR;

U.S. Pat. No. 3,650,269 EMERGENCY OXYGEN REBREATHER;

U.S. Pat. No. 3,646,934 AIR COMPRESSION EQUIPMENT FOR THERAPEUTIC USE;

U.S. Pat. No. 3,527,214 APPARATUS FOR REGENERATING A BREATHABLE GAS; and

U.S. Pat. No. 3,385,293 CLOSED CIRCUIT BREATHING APPARATUS.

SUMMARY OF THE INVENTION

It is an object of the invention to provide a lightweight, compact breathing device for firefighters.

A lightweight emergency air cooling device (EACD) comprises:

an outer body (housing, canister);

a coolant storage cylinder;

an expansion valve;

a manifold;

a mouthpiece;

a heat exchanger;

means for commencing (initiating) releasing coolant from the storage cylinder; and a coolant exhaust hose.

The EACD will save lives. Forestry fire fighters currently have no respiratory protection beyond a damp bandanna. This invention satisfies an urgent safety concern as well as a significant niche in the market.

The EACD is a lightweight, compact device that will provide 20 minutes of cooled air. This is double the maximum expected time a fire fighter would be subjected to extreme heat conditions. It is designed to be no larger than a canteen and weigh approximately 2.5 lbs. The EACD is to be used in conjunction with the Emergency Thermal Shelter (although modification could result in wider application and market). Should the fire fighters find themselves in the situation that the wildfire is about to overrun their position and escape is impossible, they would deploy and enter their Emergency Thermal Shelter and use the EACD to ensure that the air inside the shelter does not damage their lungs.

The Coolant Storage Cylinder holds liquid refrigerant under pressure. When engaged, a Very Small Aperture in the Expansion Valve opens, allowing coolant to escape and expand, thereby producing desired cooling effect. The Manifold guides coolant through the Heat Exchanger to the Coolant Exhaust Hose. Meanwhile, hot air enters the device, and flows around the heat exchanger to the Mouthpiece (Bite Valve) and to the user.

The present invention solves a long felt, critical safety problem.

The EACD would be relatively easy and inexpensive to manufacture, thereby keeping the price of the product to the consumer low. The market for the EACD is somewhere between 500,000 and 2,000,000 users. The state of California employs 50,000 forestry fire fighters per season. Rural and urban fire departments with mutual aid agreements would also need to be equipped with the EACD. The entire western U.S. is obviously a key market but other states have wildfires also (ie: Texas, Florida, New Jersey, etc.). Canada, Australia, Russia and Mediterranean Europe are other potential markets.

The EACD will reduce death and injury to forestry fire fighters who currently do not enjoy the protection of any sort of breathing apparatus.

DESCRIPTION OF THE DRAWINGS

Reference will be made in detail to preferred embodiments of the invention, examples of which are illustrated in the accompanying drawings. The drawings are intended to be illustrative, not limiting. Although the invention will be described in the context of these preferred embodiments, it should be understood that it is not intended to limit the spirit and scope of the invention to these particular embodiments. Certain elements in selected ones of the drawings are illustrated not-to-scale, for illustrative clarity.

DETAILED DESCRIPTION OF THE INVENTION

Figure 1:
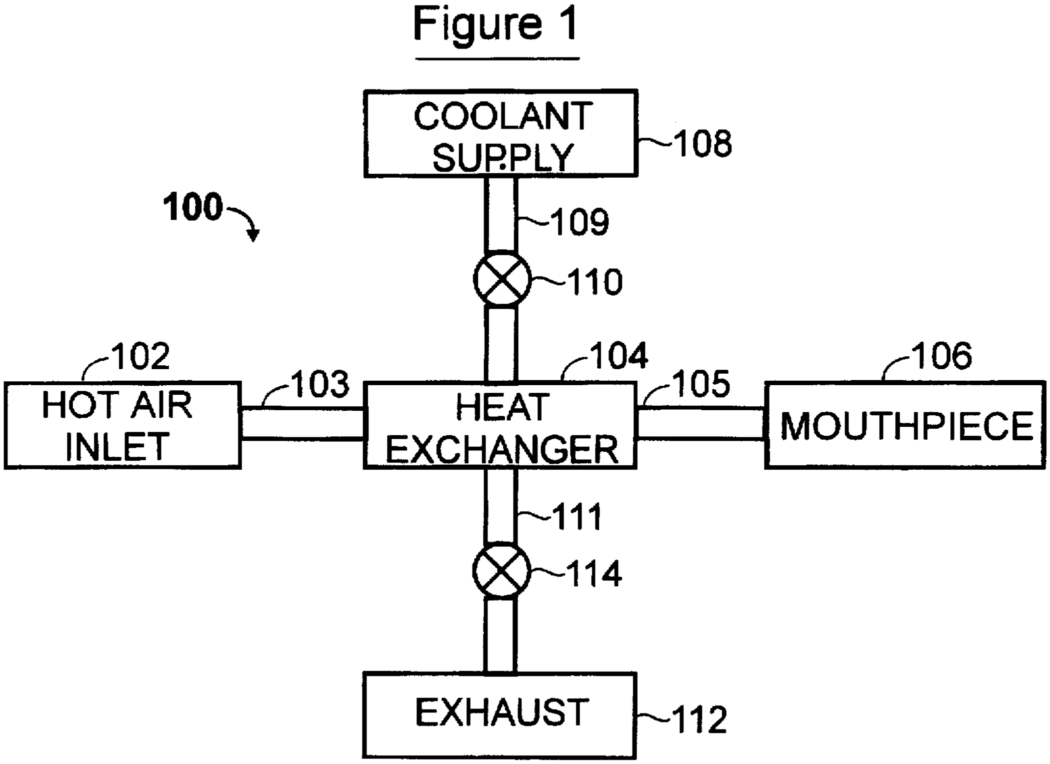
FIG. 1 is a schematic illustration of the emergency air cooling device (EACD) of the present invention.

FIG. 1 illustrates, schematically, the emergency air cooling device (EACD) 100 of the present invention.

Hot air enters a hot air inlet 102 which is in fluid communication over a line 103 with a heat exchanger 104 which, in turn, is in fluid communication over a line 105 with a mouthpiece 106.

A coolant supply 108 provides refrigerant such as pressurized carbon dioxide or freon™, or the like, via a line 109 to the heat exchanger 104. A valve 110 is disposed in the line 109. Within the heat exchanger 104, coolant from the coolant supply 108 cools air passing from the hot air inlet 103 through the heat exchanger 104 to the mouthpiece. Expended coolant is discharged through a line 111 to an exhaust port 112. An outlet orifice 114 may be disposed in the line 111 to regulate the amount of coolant that flows through the heat exchanger 104.

Coolant passing through the lines 109 and 111 is isolated within the heat exchanger 104 from air passing through the lines 103 and 105 through the heat exchanger.

In use, generally, a user inserts the mouthpiece 106 in their mouth and turns on the coolant supply (turns on the valve 110). In this manner, the user breathes air entering the hot air inlet 102 which passes through the heat exchanger and is cooled, for breathing. As described in further detail hereinbelow, the valve 110 constitutes a portion of means for commencing releasing coolant from the storage cylinder.

Figure 2:
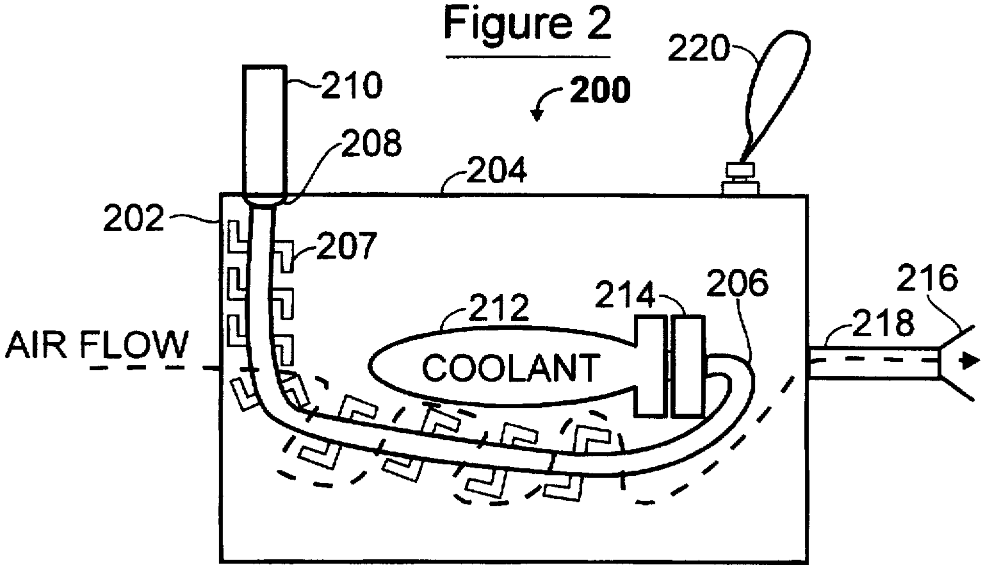
FIG. 2 is a side cross-sectional view of an embodiment of the EACD of the present invention.

FIG. 2 shows a construction of an embodiment of an EACD 200, according to the invention. Hot air enters an inlet end (left, as viewed) 202 of a housing 204. A plurality (one of many shown) of fluid passageways 206 are disposed within the housing 204, and constitute a heat exchanger (compare 104). Air passing through the housing 204 passes around the external surfaces (e.g., fins 207) of the fluid passageways 206, and exits the opposite end 208 of the housing 204. This is shown by the dashed line labeled "Air Flow".

A one end of the heat exchanger is in fluid communication with an exhaust port 208 (compare 112) which may optionally be fitted with an orifice (not shown, compare 114). Preferably, a coolant exhaust hose 210 is connected to the exhaust port 208, and is of sufficient length (e.g., 6 feet long) so that expended coolant is exhausted at a distance from the user, preferably outside of the shelter tent so that it is not breathed by the user.

An opposite end of the heat exchanger is in fluid communication with a coolant storage cylinder 212 (compare 108), and an expansion valve 214 (compare 110) is disposed between the coolant storage cylinder and the opposite end of the heat exchanger.

A mouthpiece 216 (compare 106) is fitted to the outlet end 208 of the housing 204, preferably via a cooled air supply tube 218.

In use, when the expansion valve 214 is opened, coolant flows through the fluid passageways 206 from the coolant storage cylinder 212 to the exhaust port 206, and cools (lowers the temperature of) hot air flowing through the housing 204, past the fluid passageways 206, to the mouthpiece 216.

In use, the firefighter would find a place to set up their tent, deploy the tent, remove the EACD from a pouch or the like where it is stored, hang it around his neck and, when the breathing air becomes dangerously hot, insert the mouthpiece into his mouth and initiate the flow of coolant through the heat exchanger. To this we end, a lanyard 220 is provided which has a loop of sufficient length to fit over the firefighter's head.

Initiating Coolant Flow

There are a number of ways in which the expansion valve can be operated to commence (initiate) the flow of coolant from the coolant storage cylinder, through the fluid passageways (heat exchanger) 206, to the exhaust port 208.

Figure 3:
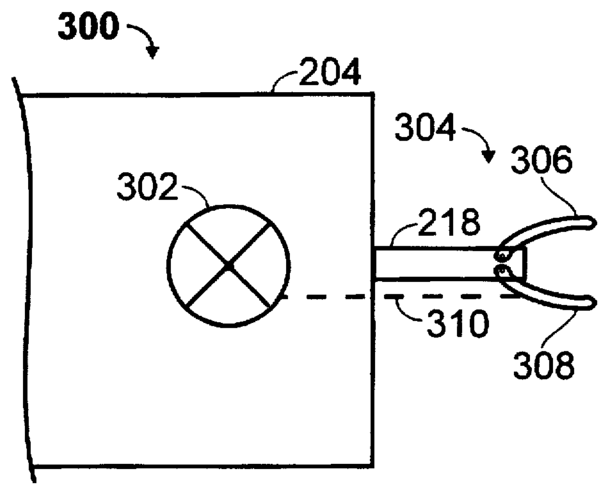
FIG. 3 is a schematic illustration of a one technique for initiating coolant flow, according to the invention.

FIG. 3 illustrates a one suitable technique for initiating the flow of coolant. In this embodiment, the valve 302 (compare 110, 214) is opened when the user bites down on the mouthpiece 304 (compare 216, 106). The mouthpiece 304 has an articulated end, comprising two clamshell type portions 306 and 308. A linkage 310, such as a cable is provided between one of the clamshell halves (308) and the valve 302. In this manner, when the user bites down on the mouthpiece 304, the valve 302 opens. Preferably, the valve 302 stays open, rather than having the user bite down on the mouthpiece each and every time it is desired to open the valve 302 and having the valve close again between "bites", but the latter is also possible and included in the scope of this invention.

Figure 4:
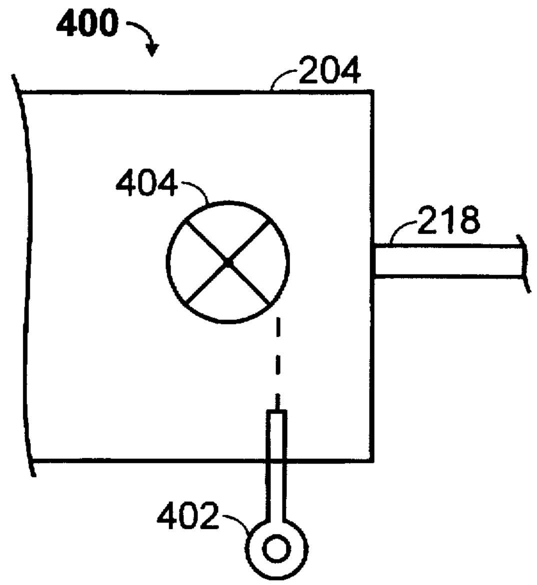
FIG. 4 is a schematic illustration of another technique for initiating coolant flow, according to the invention.

FIG. 4 illustrates another suitable technique for initiating the flow of coolant. In this embodiment 400, the valve (110, 214) is opened when the user pulls a pin which was keeping the valve closed.

A pin 402 is provided extending from outside the housing 204 to within the housing 204 and is linked to the valve 404 (compare 302). In the manner, when the user pulls the pin 402, the valve 404 opens, allowing coolant to flow through the heat exchanger.

Figure 5:
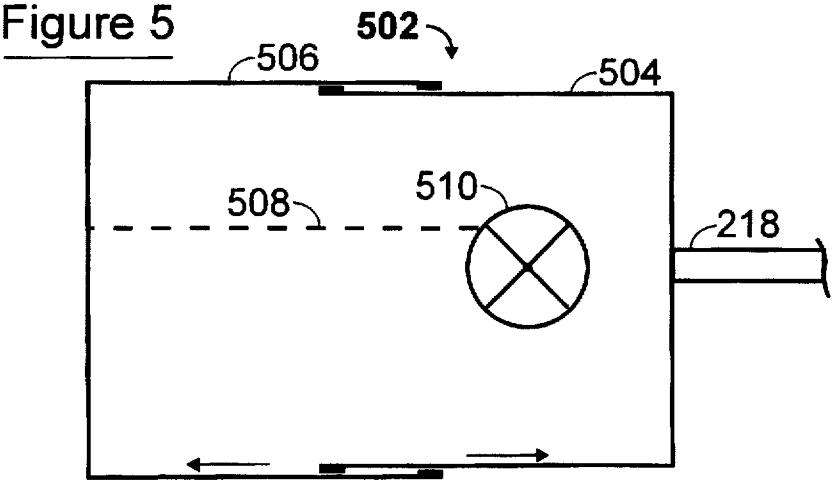
FIG. 5 is a schematic illustration of another technique for initiating coolant flow, according to the invention.

FIG. 5 illustrates another suitable technique for initiating the flow of coolant. In this embodiment, the housing 502 (compare 204) is normally collapsed, and the valve (110, 214) is opened when the user pulls the housing apart to un-collapse it. In this example, the housing 502 (compare 204) has two telescoping parts: an inner part 504 and an outer part 506. A mechanical linkage 508 such as a cable is provided between the outer part 506 and the valve 510 (compare 404). In much the same manner as pulling the pin (402) in the previous embodiment, when the user pulls the two halves 504 and 506 of the canister apart (as indicated by the opposite facing arrows), the valve 510 is opened, allowing coolant to flow.

In the embodiments described hereinabove, it is evident that the valve (302, 404, 510) is secured within the canister (housing) so that it may be opened by applying a force, via a linkage, thereto, whether by biting the mouthpiece (FIG. 3), pulling a pin (FIG. 4) or telescoping the canister (FIG. 5).

The fluid passageways (206) comprising the heat exchanger can be formed of thin plastic films, such as kapton™ or mylar™ having a plurality of fluid passageways, and manifolds for joining together all of the one ends and all of other ends of a plurality of fluid passageways so formed therein. Serpentine, interleaved patterns of fluid passageways are readily formed. In an embodiment where the canister (housing) is telescoping (compare 502), the heat exchanger can be deployed from a folded configuration to an expanded configuration upon pulling the two canister halves apart from one another.

Although the invention has been illustrated and described in detail in the drawings and foregoing description, the same is to be considered as illustrative and not restrictive in character—it being understood that only preferred embodiments have been shown and described, and that all changes and modifications that come within the spirit of the invention are desired to be protected. Undoubtedly, many other "variations" on the "themes" set forth hereinabove will occur to one having ordinary skill in the art to which the present invention most nearly pertains, and such variations are intended to be within the scope of the invention, as disclosed herein.

For example, the means for initiating flow of the coolant through the heat exchanger can be arranged so that coolant flows only when the user is biting down on the mouthpiece, and does not flow with the user is not biting down on the mouthpiece.

What is claimed is:

1. An emergency air cooling device comprising:

a housing having a one end for receiving hot air;

a coolant storage cylinder disposed within the housing;

an expansion valve in fluid communication with the coolant storage cylinder;

a heat exchanger disposed within the housing having a one end in fluid communication with the expansion valve and having another opposite end;

a coolant exhaust port in fluid communication with the opposite end of the heat exchanger for discharging expended coolant from the device;

a mouthpiece in fluid communication with the housing; and means for commencing initiating releasing coolant from the storage cylinder through the heat exchanger;

wherein air passing through the housing from the one end to the mouthpiece through the heat exchanger is cooled by coolant passing from the coolant storage cylinder through the heat exchanger.

2. An emergency air cooling device, according to claim 1, further comprising:

a coolant exhaust hose connected to the coolant exhaust port.

3. An emergency air cooling device, according to claim 2, wherein:

the coolant exhaust hose is of sufficient length to ensure that expended coolant is exhausted at a sufficient distance from a user of the device so that it is not breathed by the user.

4. An emergency air cooling device comprising:

a housing having a one end for receiving hot air;

a coolant storage cylinder disposed within the housing;

an expansion valve in fluid communication with the coolant storage cylinder;

a heat exchanger disposed within the housing having a one end in fluid communication with the expansion valve and having another opposite end;

a coolant exhaust hose in fluid communication with the opposite end of the heat exchanger;

a mouthpiece in fluid communication with the housing; and means for commencing initiating releasing coolant from the storage cylinder through the heat exchanger;

wherein air passing through the housing from the one end to the mouthpiece through the heat exchanger is cooled by coolant passing from the coolant storage cylinder through the heat exchanger; and wherein the means for commencing comprises:

further comprising:

a linkage provided between the mouthpiece and the valve.

5. An emergency air cooling device, according to claim 4, wherein:

the mouthpiece has an articulated end, comprising two clamshell type portions; and the linkage is provided between one of the two clamshell halves of the mouthpiece and the valve.

6. An emergency air cooling device comprising:

a housing having a one end for receiving hot air;

a coolant storage cylinder disposed within the housing;

an expansion valve in fluid communication with the coolant storage cylinder;

a heat exchanger disposed within the housing having a one end in fluid communication with the expansion valve and having another opposite end;

a coolant exhaust hose in fluid communication with the opposite end of the heat exchanger;

a mouthpiece in fluid communication with the housing; and means for commencing initiating releasing coolant from the storage cylinder through the heat exchanger;

wherein air passing through the housing from the one end to the mouthpiece through the heat exchanger is cooled by coolant passing from the coolant storage cylinder through the heat exchanger;

wherein:

the means for commencing comprises:

a pin extending from outside the housing to within the housing and linked to the valve.

7. An emergency air cooling device comprising:

a housing having a one end for receiving hot air;

a coolant storage cylinder disposed within the housing;

an expansion valve in fluid communication with the coolant storage cylinder;

a heat exchanger disposed within the housing having a one end in fluid communication with the expansion valve and having another opposite end;

a coolant exhaust hose in fluid communication with the opposite end of the heat exchanger;

a mouthpiece in fluid communication with the housing; and means for commencing initiating releasing coolant from the storage cylinder through the heat exchanger;

wherein air passing through the housing from the one end to the mouthpiece through the heat exchanger is cooled by coolant passing from the coolant storage cylinder through the heat exchanger;

wherein:

the housing is a two-part telescoping canister;

the valve is secured in a one of the two parts of the housing; and a linkage extends between the other of the two parts of the housing to the valve.

* * * * *